United States Patent [19]

Habermeier et al.

[11] 4,052,366
[45] Oct. 4, 1977

[54] NEW POLYGLYCIDYL COMPOUNDS CONTAINING N-HETEROCYCLIC STRUCTURE

[75] Inventors: Jürgen Habermeier, Pfeffingen; Hans Batzer, Arlesheim; Daniel Porret, Binningen, all of Switzerland

[73] Assignee: Ciba-Geigy Corporation, Ardsley, N.Y.

[21] Appl. No.: 582,041

[22] Filed: May 29, 1975

Related U.S. Application Data

[62] Division of Ser. No. 371,449, June 19, 1973, Pat. No. 3,900,493.

[30] Foreign Application Priority Data

June 23, 1972 Switzerland ............ 9528/72

[51] Int. Cl.² ................... C08G 59/04; C08G 59/26
[52] U.S. Cl. ................ 260/63 R; 260/2 EC; 260/2 N; 260/2 EP; 260/47 EA; 260/47 EC; 260/47 EN; 260/78.3 R; 260/78.41; 548/309
[58] Field of Search .......... 260/2 EP, 2 N, 2 EC, 260/47 EP, 47 EC, 47 N, 47 EA, 63 R, 78.3 R, 78.41, 309.5

[56] References Cited

U.S. PATENT DOCUMENTS

| 3,733,282 | 5/1973 | Habermeier et al. ........ 260/830 TW |
| 3,799,894 | 3/1974 | Porret et al. ........ 260/2 EP |
| 3,809,660 | 5/1974 | Habermeier et al. ........ 260/2 EP |
| 3,813,352 | 5/1974 | Habermeier et al. ........ 260/2 EP |

Primary Examiner—Harold D. Anderson
Assistant Examiner—E. A. Nielsen
Attorney, Agent, or Firm—Vincent J. Cavalieri

[57] ABSTRACT

The polyglycidyl compounds according to the invention can be manufactured by reacting epihalogenohydrin with compounds of the formula IV

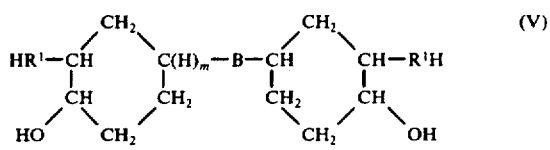

or the formula V

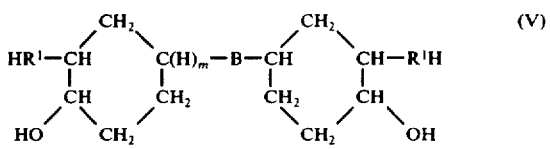

in which (1) $n$ denotes 2, 3 or 4, (2) A represents a 2-valent, 3-valent or 4-valent organic radical which either contains a N-heterocyclic or cycloaliphatic ring or 2 N-heterocyclic rings or 2 phenylene rings, (3) either D denotes the —$CH_2.O.CO$— radical and $m$ denotes the number 1, or D denotes the radical

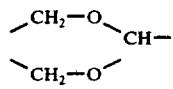

and $m$ denotes 0, and (4) $R^1$ represents a divalent radical, which contains at least one hydantoin ring or uracil ring. During the reaction hydrogen halide splits off. From curable mixtures containing polyglycidyl compounds according to the invention and a curing agent such as hexahydrophthalic anhydride or phthalic anhydride are obtained products with good mechanical and electrical properties.

9 Claims, No Drawings

POLYGLYCIDYL COMPOUNDS CONTAINING N-HETEROCYCLIC STRUCTURE

This is a divisional of application Ser. No. 371,449 filed on June 19, 1973, now Patent No. 3,900,493, issued Aug. 19, 1975.

The invention relates to new polyglycidyl compounds containing N-heterocyclic structures, a process for their manufacture and their use.

Heterocyclic compounds which contain glycidyl groups are known, for example from German Offenlegungsschriften Nos. 1,932,305 and 1,932,306 and from French Patent Specification No. 1,394,438 and Swiss Patent Specification No. 345,347. The process products hitherto known frequently present problems with regard to storage and are not always easy to process. Furthermore, the cured products frequently do not meet the standards set with regard to mechanical and electrical properties.

The subject of the invention are new polyglycidyl compounds containing N-heterocyclic structures, of the general formula I

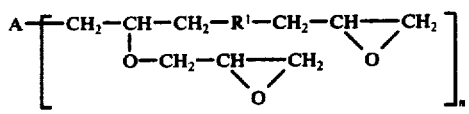  (I)

in which (1), $n$ denotes 2, 3 or 4, (2) A represents a 2-valent, 3-valent or 4-valent organic radical which either contains a N-heterocyclic or cycloaliphatic ring or 2 N-heterocyclic rings or 2 phenylene rings, and (3) $R^1$ represents a divalent radical of the formula II

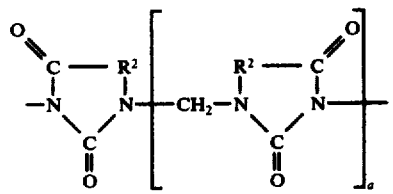

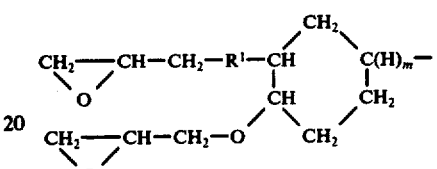 (II)

in which $a$ and $b$ are identical or different and denote either 0 or 1, and in which $R^3$ denotes a hydrogen atom or a methyl group and $R^2$ denotes a nitrogen-free, 2-valent radical which is necessary to add sufficient ring carbon atoms to complete a five-membered or six-membered unsubstituted or substituted ring, or of the general formula III

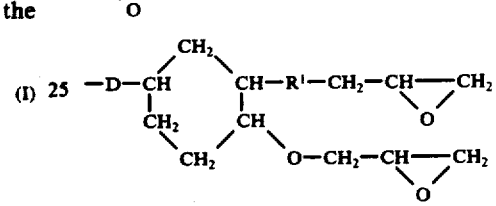 (III)

in which (1) either D denotes the —$CH_2.O.CO$— radical and $m$ denotes the number 1, or D denotes the radical

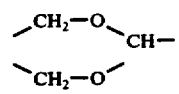

and $m$ denotes 0, and (2) $R^1$ has the above meaning.

In the formula I, A can represent one of the following organic molecular groups:

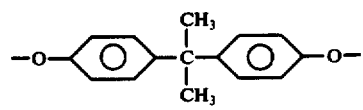

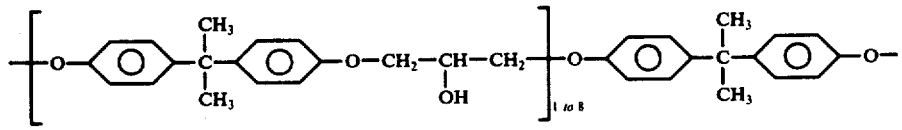

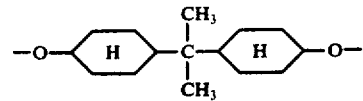

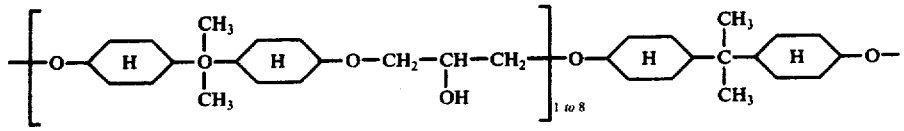

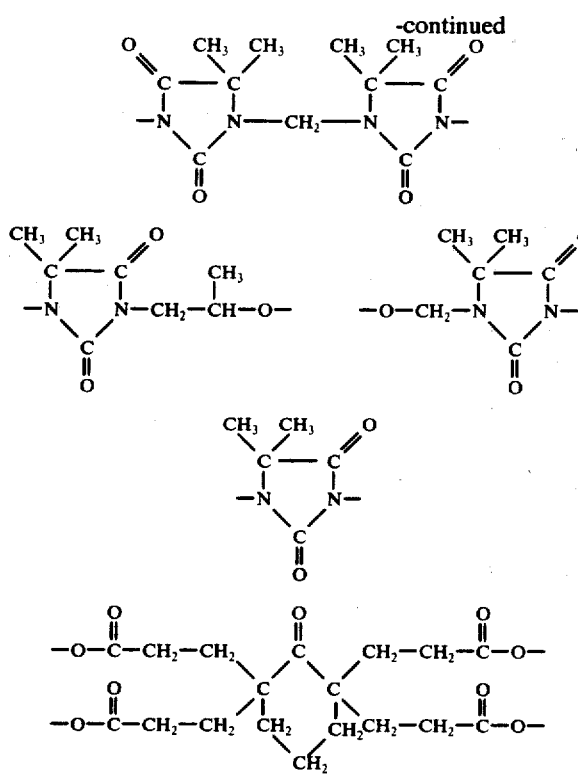

In the formula II, R² can denote one of the radicals

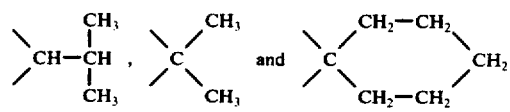

In such a case, the polyglycidyl compounds according to the formula I or formula III are substances containing hydantoin rings.

R² can, however, also represent one of the following divalent radicals:

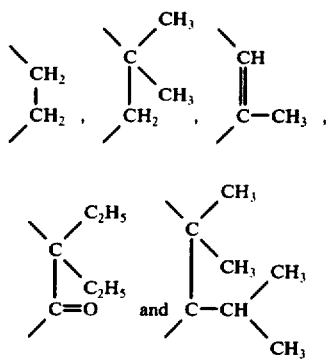

If this is the case, the polyglycidyl compounds according to the formula I or formula III are substances which contain rings which are derived from uracil or barbituric acid.

The new polyglycidyl compounds containing N-heterocyclic structures can be manufactured according to the invention in an elegant manner by reacting compounds of the formula IV or the formula V

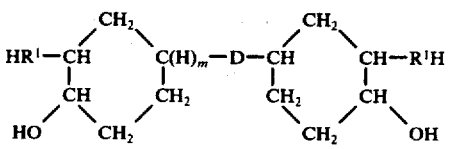

in which A, R¹, D, n and m have the abovementioned meaning, with epihalogenohydrin, hydrogen halide being split off. Instead of epihalogenohydrin, methyl epihalogenohydrin can also be employed. In that case, polyglycidyl compounds are obtained which are slightly modified by the methyl groups introduced into the molecule. Preferably, epichlorohydrin is employed.

The process according to the invention is advantageously carried out with azeotropic removal of the water in the presence of a hydrogen halide acceptor. As such it is possible to use, for example, alkali metal hydroxide, most simply sodium hydroxide in an equivalent amount or in slight excess (5 - 30%). If desired, a catalyst is also employed, for example a quaternary ammonium halide, such as tetramethylammonium hydroxide, tetraethylammonium bromide or benzyltrimethylammonium chloride.

It is surprising that the process according to the invention can be carried out without complications. Given the presence of the numerous active H atoms in the reaction mixture and the accumulation of the epoxide groups in the molecule of the resulting end product of the formula I or III, complications due to undesired polyaddition and premature crosslinking were to be expected.

The starting substances of the formula IV or of the formula V for the manufacture of the polyglycidyl compounds according to the invention are also new. They are substances which always contain at least 2 (namely n) secondary hydroxyl groups. In addition, they either contain $n > NH$ groups of a N-heterocyclic ring and $n$ primary hydroxyl groups.

The manufacture of these new polyols of the formula IV or of the formula V takes place, in the former case, by reaction of appropriate diepoxide, triepoxide or tetraepoxide compounds with H-heterocyclic substances of the formula

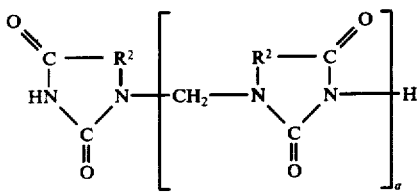

in which $R^2$ and $a$ are defined as above, to give the corresponding adduct in a manner which is in itself known, there being about $2 > NH$ groups in the reaction mixture per 1 epoxide group.

In the latter case, in which the substances of the formula IV or of the formula V also contain primary hydroxyl groups in addition to the secondary hydroxyl groups, an identical adduct to that in the first case is initially manufactured as an intermediate product. In a second stage, the $> NH$ groups contained in this adduct are then reacted further with ethylene oxide or propylene oxide in a known manner to give the particular primary alcohol.

The following may be mentioned as examples of polyepoxide compounds which are suitable for use as starting products for the polyols of the formula IV: 1-glycidyl-3-(glycidyl-2'-oxy-n-propyl)-5,5-dimethylhydantoin, 1-glycidyloxymethyl-3-glycidyl-5,5-dimethylhydantoin, 1,1'methylenebis-(3-glycidyl-5,5-dimethylhydantoin), 1,3-diglycidyl-5,5-dimethylhydantoin, 2,2,6,6-tetra(glycidylcarboxy-ethyl)cyclohexanone, bisphenol-A diglycidyl ether or polymeric derivatives thereof. (As regards the polymeric derivatives of bis-phenol-A digylcidyl ethers, it should additionally be noted that for practical purposes appropriate polymer mixtures with degrees of polymerisation of up to about 5 are concerned).

As polyepoxide compounds which are suitable for use as starting products for the polyols of the formula V, the following should be listed as examples: 3,4-epoxycyclohexylmethyl)-3,4-epoxycyclohexanecarboxylate and 3-(3',4'-epoxycyclohexyl)-2,4-dioxaspiro-(5,5)-9,10-epoxyundecane.

The following N-heterocyclic substances are examples of reaction partners for these polyepoxide compounds in the manufacture of the above polyols: 5,5-pentamethylenehydantoin, 5,5-dimethylhydantoin, 5-isopropylhydantoin, 5,5-diethylbarbituric acid, 1,1'-methylene-bis-(5,5-dimethyl-5,6-dihydrouracil), 1,1'-methylene-bis-(5,5-dimethylhydantoin), 1,1'-methylene-bis-(5-isopropylhydantoin), 6-methyluracil, 5,5-dimethyl-6-isopropyl-5,6-dihydrouracil and 1,2-bis-(5,5-dimethylhydantoinyl-3)-ethane.

These new polyols which may contain $> NH$ groups are viscous or solid, in most cases pale yellow-coloured, substances. If these are derived from polymeric bisphenol-A diglycidyl ethers, the reaction with the epihalogenohydrin leads either to polyglycidyl compounds of the formula I which still contain, unchanged, the OH groups originating from the initial digylcidyl ethers, or to polyglycidyl compounds which contain additional epoxide groups produced by reaction of these originally present OH groups with epihalogenohydrin. Furthermore, intermediate stages are also possible. The degree of reaction of the original OH groups results essentially from the amount of the epihalogenohydrin and caustic alkali in the reaction mixture. Usable polyglycidyl compounds of the formula (I) according to the invention are also obtained by starting from compounds of the formula IV in which the radical A denotes the molecular group of the formula

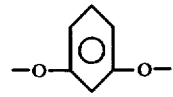

or the molecular group of the formula

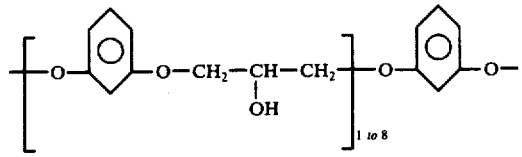

Starting substances for these special compounds of the formula IV are again the diglycidyl ethers of resorcinol or of polyethers containing several resorcinol structures.

The polyglycidyl compounds according to the invention, of the formula I and the formula III, are solid or liquid, mostly pale yellow-coloured, substances. The special feature of these substances is that they contain a relatively large number of glycidyl groups per molecule. They have epoxide contents of between about 3.0 and 8.0 mols/kg of resin and can, together with curing agents, such as dicarboxylic acid anhydrides, easily be converted into curable mixtures at temperatures of 60° – 160° C. Hexahydrophthalic anhydride and phthalic anhydride are particularly suitable as curing agents.

The curing of these mixtures, which is a further subject of this invention, in general takes place at temperatures of 80° to 170° C. It can also be carried out stepwise at different temperatures. Ultimately, mouldings of high mechanical and electrical quality are obtained. The curable mixtures according to the invention are in particular suitable for use as compression moulding compositions and casting resins. In principle, they can also be used as lacquer resins and laminating resins.

For the manufacture, modification or processing and the like, everything known to the expert from publications and relevant patent specifications on an extensive scale applies to the mixtures according to the invention.

In the examples which follow, parts denote parts by weight and the percentages denote percentages by weight. The relationship of parts by volume to parts by weight is as of ml to g.

A. Manufacturing Examples

Manufacture of the Starting Substances according to the Formula IV or V

EXAMPLE A

Adduct of 5,5-dimethylhydantoin and 1,1'-methylene-bis-(3-glycidyl-5,5-dimethylhydantoin)

256 g of 5,5-dimethylhydantoin (2 mols) and 1.6 ml of 40% strength aqueous tetramethylammonium chloride solution are heated to 170° C in a glass apparatus equipped with a stirrer, thermometer and reflux condenser and the resulting melt is stirred. 380 g of 1,1'-methylene-bis-(3-glycidyl-5,5-dimethylhydantoin) (5.0 equivalent of epoxide) are added over the course of one hour, whilst stirring. 3 hours later, the residual epoxide content is only 0.14 equivalent/kg. The mixture is stirred for a further 5 hours at 190° C and the adduct is poured out onto a metal sheet. A solid, clear, brittle mass of softening point 116° C is obtained in quantitative yield. The residual epoxide content is only 0.048 equivalent/kg (corresponding to 98.3% conversion).

The content of >NH groups in the 3-position of the N-heterocyclic ring is 0.17 equivalent/kg (corresponding to a conversion of 94.3% of theory). Accordingly, the product predominantly consists of:

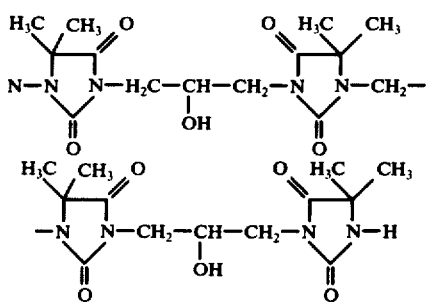

EXAMPLE B

Adduct of 5,5-dimethylhydantoin and bisphenol-A-diglycidyl ether

A solution of 177 g of a technically manufactured bisphenol-A diglycidyl ether (Araldite MY 790) of high monomer content (5.70 epoxide equivalents/kg) (corresponding to 0.5 mol) in 500 ml of dimethylformamide is mixed with 128.2 g of 5,5-dimethylhydantoin (1 mol) and the mixture is heated to 120° C whilst stirring. 1.7 g of tetraethylammonium chloride are then added, whereupon a slightly exothermic reaction commences. In the course thereof, the temperature rises to 130° C. Thereafter, the mixture is stirred for a further 2 hours at 120° C adjusted to pH=7 with a little 50% strength sulphuric acid, filtered hot and concentrated at 75° C/15 mm Hg. Thereafter the residue is dried to constant weight at 90° C/0.2 mm Hg. A solid, clear, light yellow adduct is obtained in quantitative yield. This crude adduct can be purified by recrystallisation from 50% strength ethanol in the ratio 1:6. After drying, 269.8 g (88.4% of theory) of a colourless fine crystalline material which melts at 169° - 182° C is obtained. The NMR and IR spectra show that predominantly an adduct of the following structure is present:

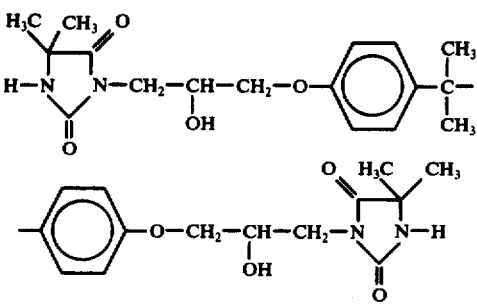

EXAMPLE C

Adduct of methylene-bis-dimethylhydantoin and bisphenol-A diglycidyl ether 117.5 g of the bisphenol-A diglycidyl ether used in Example 2 (0.3 mol) in 700 ml of dimethylformamide are reacted with 160 g of 1,1'-methylene-bis(5,5-dimethylhydantoin) (0.6 mol) at 120° - 124° C, analogously to Example b. 0.9 g of tetraethylammonium chloride is used as the catalyst. The reaction is again slightly exothermic. After stirring for 3 hours at 120° C, the mixture is worked up according to Example B.

320 g of a yellowish, viscous resin, which is completely dried in vacuo at 70° C, are obtained. A crude product which, according to NMR, agrees with the structure shown below, is obtained. The elementary analysis of the crude product shows:

| Found | Calculated |
|---|---|
| 58.6% C | 58.9% C |
| 6.8% H | 6.4% H |
| 12.8% N | 12.8% N |

This product was again processed as it stands.

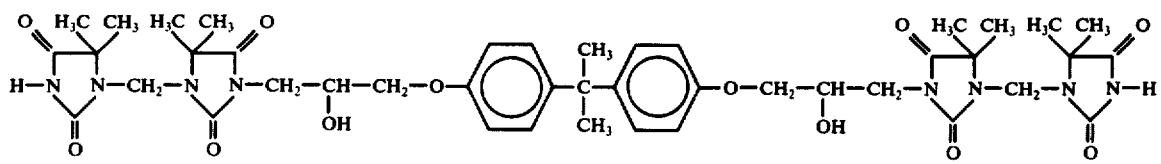

EXAMPLE D

Adduct of 5,5-dimethylhydantoin and (3,4-epoxycyclohexyl-methyl)-3,4-epoxycyclohexanecarboxylate A solution of 128 g of technically manufactured (3,4-epoxy-cyclohexylmethyl)-3,4-epoxycyclohexanecarboxylate (corresponding to 0.5 mol) in 300 ml of dimethylformamide is mixed, at 120° C, with 1.7 g of tetraethylammonium chloride and 128.1 g of 5,5-dimethylhydantoin (1.0 mol). The solution is stirred for 10 hours at 135° C and is worked up as described in Example B. A clear, light ochre-coloured product is obtained in quantitative yield; it can easily be powdered and essentially corresponds to the following structure:

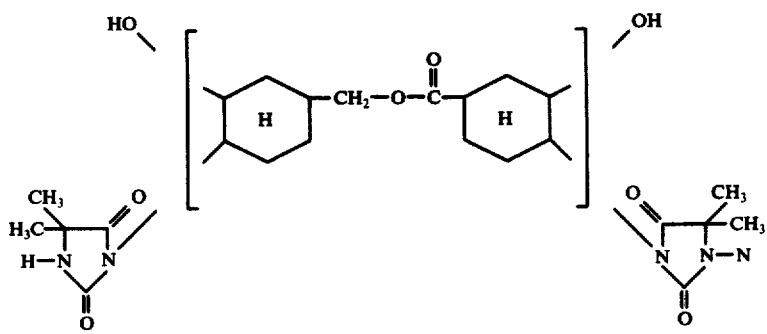

EXAMPLE E

Adduct of 1,1'-methylene-bis-dimethylhydantoin and (3,4-epoxycyclohexylmethyl)-3,4-epoxycyclohexanecarboxylate Analogously to Example D, 384 g of the epoxide resin used in Example D, in 2,000 ml of dimethylformamide, are reacted with 804.8 g of 1,1'-methylene-bis-(5,5-dimethyl)-hydantoin, using 5 g of tetraethylammonium dimethyl-6-isopropyl-5,6-dihydrouracil (1 mol) and 0.5 g of 50% strength sodium hydroxide solution is heated to 150° C whilst stirring.

The mixture is kept at this temperature for 6 hours and is then poured out onto a metal sheet to cool.

345 g of a clear, pale yellow, brittle glass (95.6% of theory) are obtained, of residual epoxide content 0.08 equivalent/kg. The product consists essentially of the adduct of the following formula:

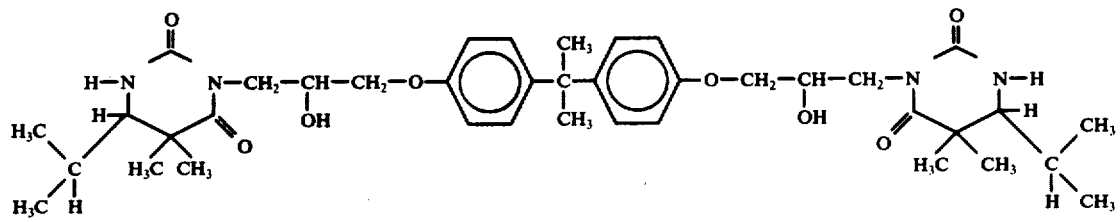

chloride as the catalyst. The reaction is carried out analogously to Example D. Working up takes place as follows: The hot solution is filtered into an Erlenmeyer flask and is left to stand at 25° C. After some hours, the adduct begins to crystallise out. The mixture is cooled to 5° C whilst stirring and 500 ml of water are added, whereby a thick crystal paste results. This is filtered and the product is suction-dried, and then dried to constant weight at 70° C under 25 mm Hg. A pale yellow crystal powder is obtained, the yield being 1,048 g (corresponding to 88.1% of theory).

EXAMPLE F

Adduct of bisphenol-A diglycid and 5,5-dimethyl-6-iso-propyl-5,6-dihydrouracil

A mixture of 177 g of the bisphenol-A diglycidyl ether used in Example B (0.5 mol), 184.2 g of 5,5-

EXAMPLE G

Adduct of higher-molecular bisphenol-A diglycidyl ether and 5,5-dimethyl-6-isopropyl-5,6-dihydrouracil A mixture of 190 g of a commercially available higher-molecular bisphenol-A glycidyl ether resin with 2.7 epoxide equivalents/kg (Araldite B), 94 g of 5,5-dimethyl-6-isopropyl-5,6-dihydrouracil and 0.5 ml of 50% strength sodium hydroxide solution is reacted at 150° C, whilst stirring. After 1.5 hours, a sample taken from the batch shows an epoxide content of 0.39 equivalent/kg. The mixture is then stirred for a further 3 hours at 165° C, in the course of which the epoxide content drops to below 0.1 equivalent/kg. The adduct is poured out onto a metal sheet to cool. An adduct mixture of predominantly the following structure is obtained:

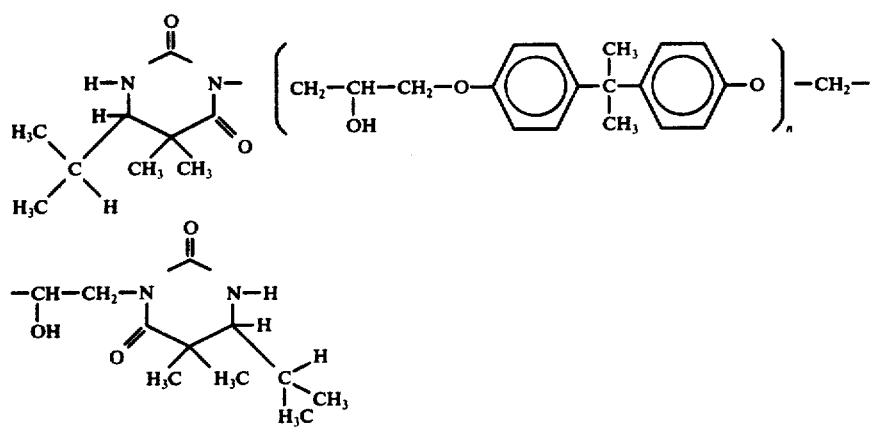

In this formula, n denotes the average degree of polymerisation (also of the initial epoxide resin) of about 6.

EXAMPLE H

Addition of ethylene oxide to the product from Example B 220 g of the adduct manufactured according to Example B (0.361 mol) and 1.4 g of lithium chloride are dissolved in 540 ml of dimethylformamide. A solution of 43.7 g of ethene oxide (0.992 mol) in 250 ml of dimethylformamide is added to the first solution at room temperature, whilst stirring gently. The mixture is warmed to 100° C over the course of 2 hours and stirred for a further 3 hours at this temperature. Thereafter it is cooled to 50° C, filtered and concentrated at 80° C/20 mm Hg, and dried to constant weight at 95° C/0.1 mm Hg. 250 g of a clear, highly viscous, light ochre-coloured polyol (100% of theory) are obtained, of which the NMR spectrum agrees with predominantly the following structure:

which the N-H groups of the formula given in Example D are very largely replaced by the structure —N—CH$_2$—CH$_2$—OH.

EXAMPLE K

Adduct of 2 mols of 5,5-diethylbarbituric acid and 1 mol of 3-(3',4'-epoxycyclohexyl)-2,4-dioxaspiro-(5,5)-9,10-epoxyundecane A solution of 64.3 g of technically manufactured 3-(3',4'-epoxycyclohexyl)-2,4-dioxaspiro-(5,5)-9,10-epoxyundecane (93.6% strength) (0.226 mol) and 0.75 g of 50% strength aqueous tetramethylammonium chloride in 250 ml of dimethylformamide is stirred at 118° C. The clear, colourless solution is mixed with 83.1 g of diethylbarbituric acid (0.452 mol) over the course of 15 minutes. This mixture is stirred for a further 10 hours at 117°–119° C and the solvent is then distilled off in vacuo. 146 g of a brown, brittle product are obtained, which melts at 67.2° C (Mettler FP 51) and has the following structure:

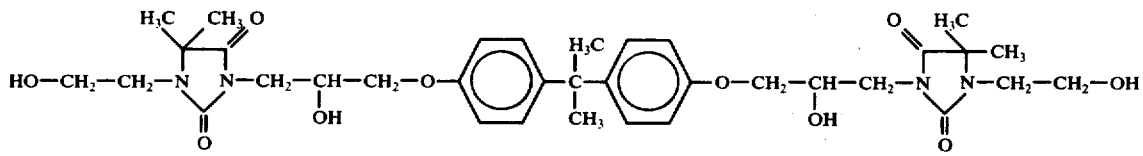

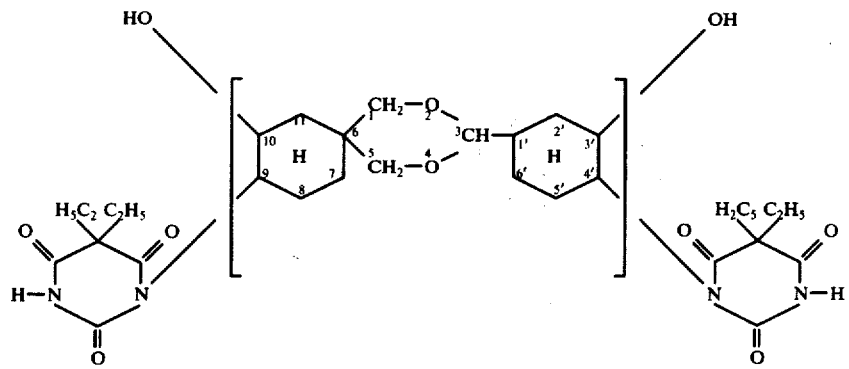

EXAMPLE I

Addition of Ethylene Oxide to the Product from Example C

Analogously to Example H, a solution of 200 g of the adduct manufactured according to Example C and 1.0 g of lithium chloride in 500 ml of dimethylformamide is treated, at room temperature, with a solution of 27.5 g of ethylene oxide in 100 ml of dimethylformamide and the procedure described in Example H is followed.

190 g of a clear glassy tetraalcohol (95% of theory) are obtained and are glycidylated in the crude form.

EXAMPLE J

Addition of Ethylene Oxide to the Product from Example D 676 g of the adduct manufactured according to Example D are dissolved in 1,300 ml of dimethylformamide. After addition of 1.7 g of lithium chloride, 234.5 g of ethylene oxide in 600 ml of dimethylformamide are added and the procedure analogous to Example H is followed. 690 g of a product (87%) are obtained, in

EXAMPLE L

Adduct of 1,3-diglycidyl-5,5-dimethylhydantoin and 5,5-dimethylhydantoin 390.9 g of technically manufactured 1,3-diglycidyl-5,5-dimethylhydantoin (92.5% strength) (1.5 mols) and 5.0 g of tetraethylammonium chloride are dissolved in 750 ml of dimethylformamide and this solution is stirred at 110° C. 384.5 g of 5,5-dimethyl-hydantoin (3.0 mols) are then added with vigorous stirring. The reaction becomes strongly exothermic so that the heating bath is removed and replaced by an ice water bath; the temperature is thus regulated to 102°–112° C. When the exothermic effect has subsided, the mixture is stirred for a further 3 hours at 115° C. The solvent is then distilled off at 100° C/30 mm Hg and the product is dried at 100° C/0.2 mm Hg. 765 g of a pale yellow, brittle glass, which can easily be powdered, are obtained.

EXAMPLE M

Adduct of 5-isopropylhydantoin and
1-glycidyl-3-glycidyl-2'-oxy-n-propyl-5,5-dimethyl-
hydantoin (molar ratio 2:1).

335 g of technically manufactured 1-glycidyl-3-glycidyloxypropyl-5,5-dimethylhydantoin (epoxide content 5.97 equivalents/kg) (1 mol) and 3.3 g of tetraethylammonium chloride are dissolved in 1 liter of dimethylformamide and 258.2 g of 5-isopropylhydantoin (2 mols) are added at 120° C, whilst stirring. The reaction becomes exothermic and the mixture is kept at 120° C for a total of 5 hours by periodic cooling. Working up takes place analogously to Example 11. 593 g (theory: 583 g) of a light brown powder, melting at 48.6° C (Mettler FP 51) are obtained. The elementary analysis of the crude product shows:

| Found | Calculated |
| --- | --- |
| 7.3% H | 7.3% H |
| 13.9% N | 14.4% N |

According to the H-NMR spectrum, the crude product only retains a trace of dimethylformamide.

The product has the following structure:

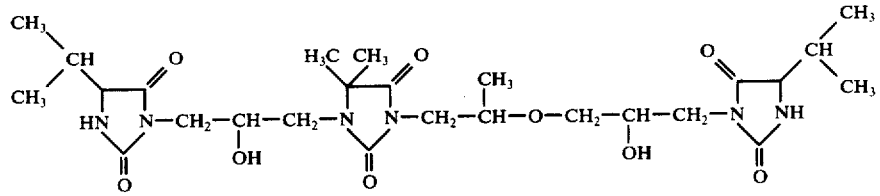

EXAMPLE N

Adduct of
1,1'-methylene-bis-(5,5-dimethyl-5,6-dihydrouracil) and
1-glycidyloxymethyl-3-glycidyl-5,5-dimethylhydantoin
(molar ratio 2 : 1)

A solution of 22.2 g of 1-glycidyloxymethyl-3-glycidyl-5,5-dimethylhydantoin (97.3% strength) (0.077 mol) and 0.2 g of tetraethylammonium chloride in 80 ml of dimethylformamide is mixed at 120° C, with 45.6 g of 1,1'-methylene-bis(5,5-dimethyl-5,6-dihydrouracil) (0.154 mol). The reaction, and working up, take place analogously to Example K.

44 g of the corresponding adduct are obtained in the form of a light powder (66.7% of theory).

EXAMPLE O

Adduct of 1,1'-methylene-bis(5,5-dimethylhydantoin)
and
1,1'-methylene-bis(3-glycidyl-5,5-dimethylhydantoin)

A mixture of 205.5 g of 1,1'-methylene-bis-(3-glycidyl-5,5-dimethylhydantoin) (4.9 epoxide equivalents/kg) (0.54 mol), 289.8 g of 1,1'-methylene-bis(5,5-dimethyl-hydantoin) (1.08 mols), 1.8 g of tetraethylammonium chloride and 750 ml of dimethylformamide is stirred at 110° - 120° C; the reaction becomes exothermic and is carried out according to Example K, and the product is worked up according to Example K.

488 g of a light yellow powder (98.6% of theory) are obtained.

EXAMPLE P

Adduct of 6-methyluracil and
1,1'-methylene-bis-(3-glycidyl-5,5-dimethylhydantoin)

A mixture of 76.1 g of the 1,1'-methylene-bis-(3-glycidyl-5,5-dimethylhydantoin) (0.2 mol) used in Example N, 0.6 g of tetraethylammonium chloride and 50.5 g of 6-methyluracil (0.4 mol) is stirred for 10 hours at 120° C, whereby a clear, colourless solution is produced; this is worked up analogously to Example K.

127 g (100% of theory) of a light yellow, glassy substance are obtained. This can be recrystallised from alcohol. 104 g (82.2% of theory) of fine crystals, melting at 176° C (Mettler FP 51) are obtained.

EXAMPLE Q

Adduct of 5,5-dimethylhydantoin and
2,2,6,6-tetra(glycidylcarboxy-ethyl)cyclohexanone 123.8 g of 2,2,6,6-tetra(glycidyl-carboxy-ethyl)-cyclohexanone (epoxide content: 5.9 equivalents/kg) (0.184 mol), 94.1 g of 5,5-dimethylhydantoin and 200 ml of dimethylformamide are stirred for 5 hours at 125° - 130° C; the reaction is initially slightly exothermic. The working up of the product takes place analogously to Example K. 210 g of a highly viscous liquid are obtained; this crude product still contains a trace of dimethylformamide.

EXAMPLE R

2:1 adduct of 1,3-diglycidyl-5,5-dimethyl-hydantoin and
hydrogenated bisphenol-A The following mixture is stirred for 4.5 hors at 120° C: 512.8 g of 1,3-diglycidyl-5,5-dimethylhydantoin (2.0 mols), 240.4 g of hydrogenated bisphenol A (1.0 mol), 3.0 g of lithium chloride and 2 l of dimethylformamide.

After the customary working up by distilling off the solvent, and drying, 746 g (103% of theory; the product still contains traces of dimethylformamide) of a light ochre-coloured melt, which crystallises, are obtained. This crude product (diglycidyl compound) has an epoxide content of 2.49 equivalents/kg (89.8% of theory) and is employed, without further purification, for the manufacture of the tetraglycidyl compound.

EXAMPLE S

2:1 adduct of 5,5-dimethylhydantoin and the diglycidyl
ether of hydrogenated bisphenol A A mixture of 454.6 g of technically manufactured diglycidyl ether of hydrogenated bisphenol A, having an epoxide content of 4.4 equivalents/kg (1.0 mol), 256.3 g of 5,5-dimethylhydantoin, 2.5 g of lithium chloride and 1.5 l of dimethylformamide is stirred for 4 hours at 130°-140° C. Thereafter it is filtered and completely concentrated at 80° C under a water pump vacuum, and the residue is then dried for 1.5 hours at 80° C/0.6 mm Hg.

A light yellow, clear, resinous adduct is obtained, which no longer contains any epoxide and still contains a little dimethylformamide; yield 750.5 g.

MANUFACTURE OF THE POLYGLYCIDYL COMPOUNDS ACCORDING TO THE INVENTION

Example 1

A mixture of 63.6 g of the adduct manufactured according to Example A (0.1 mol; 0.4 equivalent of reactive H), 370 g of epichlorohydrin and 0.3 g of tetramethylammonium chloride is stirred for 140 minutes at 117°-118° C. A sample withdrawn from the batch and freed of all volatile constituents then contains 1.88 epoxide equivalents/kg.

The dehydrochlorination is carried out as follows: An azeotropic circulatory distillation is set up, by application of vacuum (60-90 mm Hg) in such a way that a vigorous distillation proceeds in the reaction mixture at 60° C. 38.4 g of 50% strength sodium hydroxide solution (0.48 mol) are now added dropwise over the course of 150 minutes, whilst stirring vigorously. In the course thereof, the water present in the reaction mixture is continuously removed from the batch, and separated off. Thereafter, distillation is allowed to continue for a further 15 minutes, the residue is cooled to 30° C, and the sodium chloride produced in the reaction is filtered off. The filtrate is then washed with 50 ml of water to remove the last traces of caustic alkali and salt and the organic phase is concentrated on a rotary evaporator at 60° C/15 mm Hg. 50 ml of water are now added and traces of epichlorohydrin and the like are distilled off together with this water. Thereafter, the same process is repeated with 50 ml of toluene to remove remnants of water. The residue is then treated at 120° C/0.2 mm Hg until it reaches constant weight.

82.7 g (96.2% of theory) of a brittle, clear, pale yellow resin of epoxide content 4.30 equivalents/kg (92.7% of theory) are obtained. The total chlorine content is 1.1%. The new tetraglycidyl compound has a softening point of 66° C (according to Kofler) and essentially is present in the following structure: Example 1). 632 g (97% of theory) of a very viscous tetraglycidyl compound are obtained, of epoxide content 4.26 epoxide equivalents/kg (86.4% of theory).

Example 3

Glycidylation of the Adduct According to Example I 179.8 g of the crude tetraalcohol manufactured according to Example I (0.186 mol) are treated with 552 g of epichlorohydrin (5.967 mols) and 0.9 g of tetraethylammonium chloride analogously to Example A). The dehydrochlorination is carried out with 77.8 g of 50% strength sodium hydroxide solution, again as described. After working up and purification analogously to Example 1), 189.2 g of a very viscous, clear, light yellow tetraglycidyl compound (94% of theory) are obtained, of which the epoxide content is 3.4 epoxide equivalents/kg (100% of theory). The total chlorine content is 2%.

Example 4

Glycidylation of the Adduct According to Example J 656.5 g of the tetraalcohol obtained according to Example J (1.1 mols) and 4 g of tetraethylammonium chloride in 3,330 g of epichlorohydrin (36.0 mols) are treated analogously to Example 1. The dehydrohalogenation is carried out with 456.6 g of 50% strength aqueous sodium hydroxide solution (5.71 mols) in the manner described above. The working up again takes place analogously to Example A). 704 g (78% of theory) of the desired tetraglycidyl compound, of which the epoxide content is 4.69 epoxide equivalent per kg (95.8% of theory), are obtained. The total chlorine content is 1.6%. The nitrogen content is 6.7% (theory, 6.9%).

Example 5

Glycidylation of the Adduct from Example E 789 g of the adduct manufactured according to Example E (1 mol) together with 6.6 g of tetraethylammonium chloride are treated with 2,950 g of epichlorohydrin according to Example 1. Both the dehydrochlorination with 410 g of 50% strength aqueous sodium

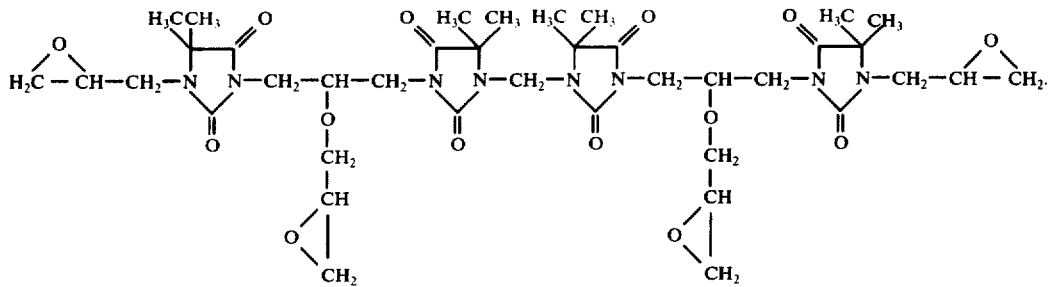

EXAMPLE 2

Glycidylation of the Adduct According to Example B

Analogously to Example 1, 503 g of the adduct manufactured according to Example B (0.84 mol) are stirred with 2,495 g of epichlorohydrin (26.97 mols) and 5.6 g of tetraethylammonium chloride for 3 hours at 90° C. Thereafter, dehydrochlorination is carried out, as described in Example 1), with 350.5 g of 50% strength sodium hydroxide solution, under azeotropic circulatory distillation and whilst stirring vigorously. Working up and purification are also carried out analogously to hydroxide solution and the subsequent working up are also carried out according to Example 1. 951 g (95% of theory) of a solid, clear resin with 3.32 epoxide equivalents/kg (82.6% of theory) are obtained. The softening range is about 92° C.

Example 6

Glycidylation of the Adduct from Example F

As described in Example 1, 345 g of the adduct from Example F, 3.2 g of tetraethylammonium chloride, 1,420 g of epichlorohydrin and 199.5 g of 50% strength aqueous sodium hydroxide solution are reacted, and worked up, under the conditions described.

383.2 g of the desired tetraglycidyl compound (94.8% of theory), containing 4.08 epoxide equivalents/kg (86% of theory), are obtained. The softening point is about 58° C.

Example 7

Glycidylation of the Adduct from Example G 182 g of the adduct manufactured according to Example G are treated with 1.3 g of tetraethylammonium chloride and 1,200 g of epichlorohydrin according to Example 1. The dehydrochlorination with 67.3 g of 50% strength aqueous sodium hydroxide solution, and the further working up, also take place as described above.

216.2 g of a solid resin (99% of theory) with an epoxide content of 3.8 equivalents/kg are obtained.

Example 8

Tetraglycidyl Compound of the Product According to Example H

Analogously to Example 1, a solution of 139.4 g of the tetraalcohol manufactured according to Example H (0.2 mol) is reacted with 444 g of epichlorohydrin (4.8 mols) and 0.9 g of tetraethylammonium chloride by first stirring for 2 hours at 90° C.

Dehydrohalogenation is then carried out with 83.5 g of 50% strength sodium hydroxide solution under azeotropic circulatory distillation, as described in more detail in Example 1. The working up and purification of the product take place according to Example 1.

170.7 g of a yellow, clear, viscous resin (93.9% of theory), of epoxide content 4.35 equivalents/kg (98.9% of theory), are obtained. The total chlorine content is 1.5%.

Example 9

Tetraglycidyl Compound of the Product According to Example K

A solution of 137.7 g of the adduct manufactured according to Example K, of melting point 67.2° C (0.217 mol) and 1.9 g of 50% strength aqueous tetraethylammonium chloride solution in 642 g of epichlorohydrin (6.94 mols) is treated analogously to Example 1. The dehydrohalogenation also takes place according to Example 1, with 79.9 g of 50% strength aqueous sodium hydroxide solution (0.998 mol). After working up analogously to Example 1, 135.4 g (72.6% of theory) of a yellow, practically solid (softening point about room temperature) tetraglycidyl compound of epoxide content 4.57 equivalents/kg (98.1% of theory) are obtained. Analytical data:

| Found | Calculated ($C_{43}H_{62}N_4O_{14}$) |
|---|---|
| 7.4% H | 7.3% H |
| 6.7% N | 6.5% N |
| 1.4% Cl | 0.0% Cl |

Example 10

Tetaglycidylation of the Product According to Example L 621 g of the adduct manufactured according to Example L (1.25 mols) are treated analogously to Example 1 with 3,700 g of epichlorohydrin, 10 g of 50% strength aqueous tetramethylammonium chloride solution and then with 460 g of 40% strength aqueous sodium hydroxide solution (5.75 mols); the working up of the product is carried out appropriately.

762.2 g (84.6% of theory) of a brown tetraglycidyl compound with 4.96 epoxide equivalents/kg (89.3% of theory) and 1.2% of total chlorine, which softens at room temperature, are obtained.

Example 11

Tetraglycidylation of the Product According to Example M

The following substances are reacted analogously to Example 1): 563.0 g of the adduct from Example M (0.966 mol), 2,860 g of epichlorohydrin (30.9 mols), 8.5 g of 50% strength aqueous tetramethylammonium chloride and 356 g of 50% strength aqueous sodium hydroxide solution.

Working up takes place as described above and a highly viscous brown resin, of epoxide content 4.37 equivalents/kg (88.1% of theory), is obtained in 92% yield (715.7 g); the total chlorine content is 2%.

Example 12

Tetraglycidylation of the Product According to Example N

The following are reacted analogously to Example 1: 36 g of the adduct from Example N (0.042 mol), 124 g of epichlorohydrin (1.34 mols), 0.7 g of 50% strength aqueous tetramethylammonium chloride and 15.4 g of 50% strength aqueous sodium hydroxide solution (0.19 mol).

After the customary working up, 28 g (62%) of a light brown, tacky resin are obtained. Epoxide content 3.08 equivalents/kg (83% of theory).

Example 13

Tetraglycidylation of the Product According to Example O

The following are reacted according to Example 1: 0.315 mol of adduct according to Example O (289 g), 10 mols of epichlorohydrin (925 g), 2.8 g of 50% strength aqueous tetramethylammonium chloride and 1.45 mols of 50% strength sodium hydroxide solution (116 g). Working up takes place as mentioned and a light yellow, solid tetraglycidyl compound is obtained, of softening point 67° C (according to Kofler). The epoxide content is 3.71 equivalents/kg (94.6% of theory).

Example 14

Tetraglycidyl Compound of the Product According to Example C

The following were reacted analogously to Example 1: 444.6 g of adduct, manufactured according to Example C (0.5 mol), 1,480 g of epichlorohydrin (16 mols), 8.8 g of 50% strength aqueous tetramethylammonium chloride and 184 g of 50% strength sodium hydroxide solution (2.3 mols).

The product is isolated according to Example 1) and 441.4 g (81%) of a solid, light brown resin are obtained, softening at 78° C (Kofler) and having an epoxide content of 3.41 equivalents/kg (93.9% of theory).

Example 15

Tetraglycidyl Compound of the Product According to Example P

The following are reacted analogously to Example 1: 72.0 g of the adduct according to Example P (0.114 mol), 474.0 g of epichlorohydrin (5.125 mols), 4.6 g of tetramethylammonium chloride, 50% strength in water and 42.4 g of 50% strength aqueous sodium hydroxide solution (0.53 mol).

The customary working up yields 76.0 g (77.9% of theory) of the tetraglycidyl compound of epoxide content of 3.81 equivalents/kg (81.5% of theory); the compound softens at 103° C (Kofler).

Example 16

Polyglycidyl Compound of the Product According to Example Q

The following are reacted as in Example 1: 210 g of the adduct from Example Q (0.2 mol), 1,520 g of epichlorohydrin (16.4 mols), 8 g of 50% strength aqueous tetramethylammonium chloride and 151 g of 50% strength aqueous sodium hydroxide solution (1.89 mols).

After the customary working up, 79 g of the viscous polyglycidyl compound are obtained, which according to the epoxide content (5.08 equivalents/kg) on average contain 7.98 epoxide groups per molecule (theory: 8.0).

Example 17

Glycidylation of the Adduct Manufactured According to Example R 736 g of the adduct manufactured according to Example R, having an epoxide content of 2.49 equivalents/kg (1 mol), are reacted with 2,738 g of epichlorohydrin and 10 g of 50% strength aqueous tetraethylammonium bromide, the procedure according to Example 1) being followed, and the dehydrohalogenation being carried out with 197 g of 50% strength aqueous sodium hydroxide solution, in the manner described above.

Working up also takes place according to Example L, and 302.3 g (36.3% of theory) of a clear, yellow resin of medium viscosity, of which the epoxide content corresponds to 4.68 equivalents/kg (97.5% of theory), are obtained.

Example 18

Glycidlation Glycidylation the Adduct Manufactured According to Example S

The following are reacted analogously to the description in Example 1: 750 g of the adduct according to Example S (Δ1 mol), 4,163 g of epichlorohydrin (45 mols), 20 g of tetraethylammonium chloride (50% strength, aqueous), and 400 g of 50% strength sodium hydroxide solution (5 mols).

Working up also takes place according to Example 1 and 810 g (97.2% of theory) of a highly viscous resin of epoxide content 4.07 equivalents/kg (84.8% of theory) are obtained.

B. EXAMPLES OF APPLICATIONS

Example I

48 Parts of the epoxide resin manufactured according to Example 4, with 4.69 epoxide equivalents/kg, are mixed with 55 g of hexahydrophthalic anhydride and stirred at 95° C to give a homogeneous melt. This mixture is poured into aluminium moulds of 4 mm wall thickness which have been prewarmed to 100° C and is cured in 6 hours at 100° C and 2 hours at 120° C and 10 hours at 140° C. Mouldings having the following properties are obtained:

| | | |
|---|---|---|
| Flexural strength | (VSM 77,103) | 15.8 – 16.8 kp/mm$^2$ |
| Deflection | (VSM 77, 103) | 6 – 11 mm |

Example II

64 Parts of the tetraglycidyl compound manufactured according to Example 8, containing 4.35 epoxide equivalents/kg, are mixed with 37 parts of hexahydrophthalic anhydride at 80° C and the mixture is cured in an aluminium mould of 4 mm wall thickness in 4 hours at 120° C and 15 hours at 150° C. A clear, transparent moulding having the following properties is obtained:

| | | |
|---|---|---|
| Flexural strength | (VSM 77,103) | 15.8 – 17.2 kp/mm$^2$ |
| Deflection | (VSM 77,103) | 8 – 10 mm |
| Impact strength | (VSM 77,105) | 13.3 cmkp/cm$^2$ |
| Heat distortion point according to Martens | (DIN 54,458) | 99° C |
| Water absorption | (4 days/20° C) | 0.3 – 0.4% |

Example III

100 Parts of the epoxide resin obtained according to Example 11 are mixed with 75 parts of hexahydrophthalic anhydride at 80° C to give a homogeneous melt and the mixture is cured in an aluminium mould (4 mm sheets) in 4 hours/80° C and 16 hours/140° C. The mouldings thus obtained have the following mechanical properties:

| | | |
|---|---|---|
| Flexural strength (VSM 77,103) | | 16 kp/mm$^2$ |
| Heat distortion point according to Martens | (DIN 54,458) | 146 – 147° C |
| Water absorption | (4 days/20° C) | 0.65% |

Example IV

100 Parts of the epoxide resin manufactured according to Example 11 are processed with 75 parts of hexahydrophthalic anhydride as described in Example III, and the mouldings obtained show the following properties:

| | | |
|---|---|---|
| Flexural strength (VSM 77,103) | | 14 – 36 (mean value from 5 measurements = 24) kp/mm$^2$ |
| Heat distortion point according to Martens | (DIN 54,458) | 119 – 122° C |
| Water absorption | (4 days/20° C) | 0.6% |

Example V

100 Parts of epoxide resin from Example 9 are treated with 70 parts of hexahydrophthalic anhydride according to Example III. Castings having the following properties are obtained:

| | | |
|---|---|---|
| Flexural strength (VSM 77,103) | | 23.0 kp/mm$^2$ |
| Heat distortion point according to Martens | (DIN 54,458) | 125 – 126° C |
| Water absorption | (4 days/20° C) | 0.44% |
| | (1 hour/100° C) | 0.41% |

What we claim is:

1. A curable mixture containing one or more compounds of the formula I

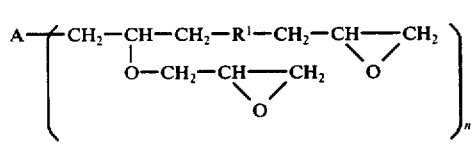 (I)

in which n denotes 2, 3 or 4, A represents a 2-valent, 3-valent or 4-valent organic radical which either contains a N-heterocyclic or cycloaliphatic ring or 2 N-heterocylic rings or 2 phenylene rings, and R¹ represents a divalent radical of the formula II

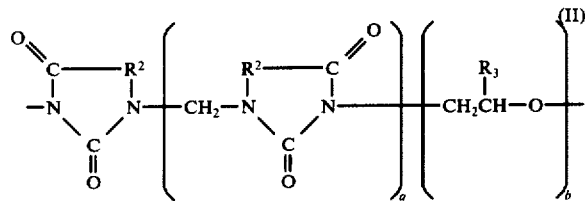 (II)

in which a and b are identical or different and denote either 0 or 1, and in which R³ denotes a hydrogen atom or a methyl group and R² denotes a nitrogen-free 2-valent radical which is necessary to add sufficient ring carbon atoms to complete a five-membered or six-membered ring, or of the general formula III

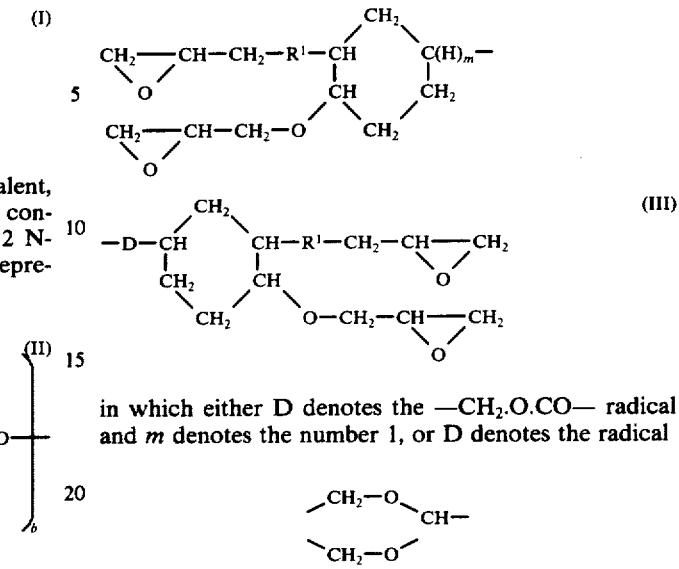 (III)

in which either D denotes the —CH₂.O.CO— radical and m denotes the number 1, or D denotes the radical $$\begin{array}{c} CH_2-O \\ \quad\quad\quad CH- \\ CH_2-O \end{array}$$

and m denotes 0, and R¹ has the above meaning; and an epoxy resin curing agent.

2. The curable mixture according to claim 1, characterised in that A in the formula I denotes one of the radicals

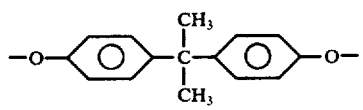

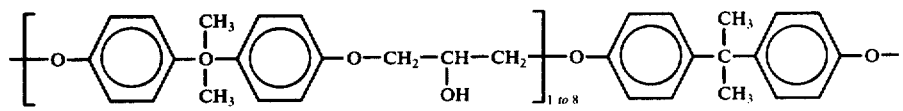

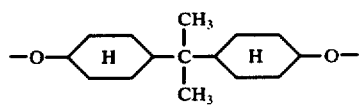

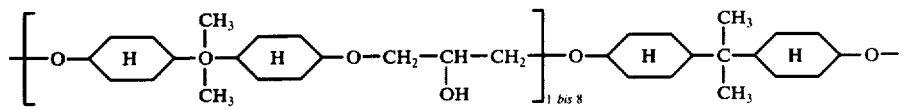

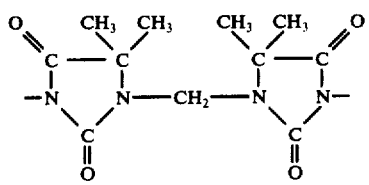

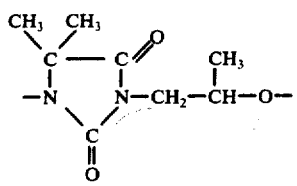

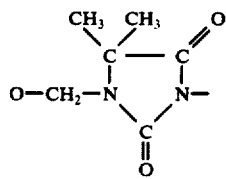
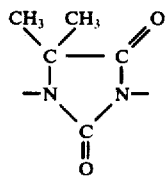
and
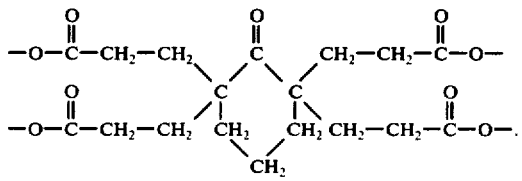
3. The curable mixture according to claim 1, characterised in that $R^2$ in the formula II denotes one of the radicals
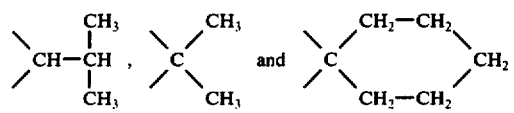
4. The curable mixture according to claim 1 wherein the polyglycidyl compound is
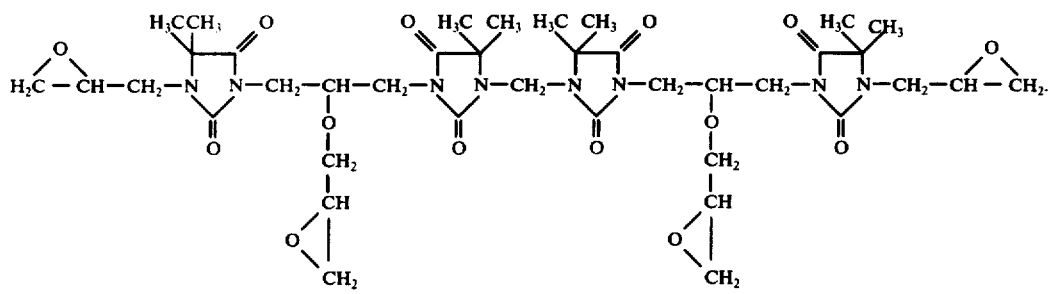
5. The curable mixture according to claim 1 wherein the polyglycidyl compound is
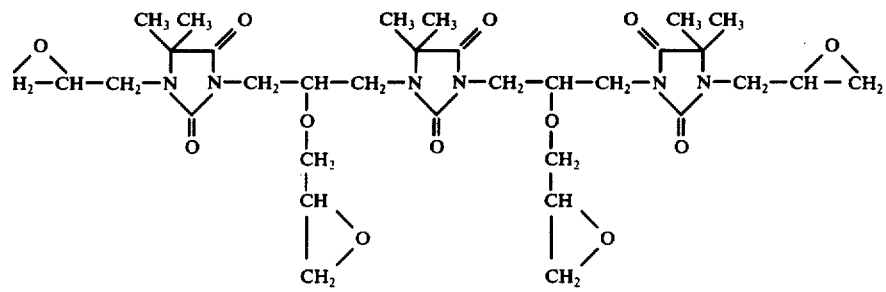
6. The curable mixture according to claim 1 wherein the polyglycidyl compound is

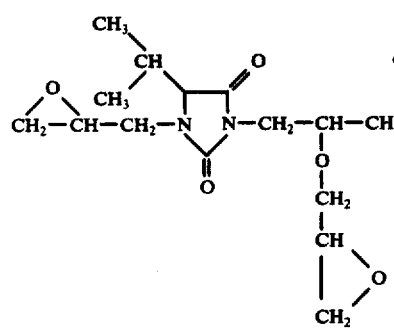
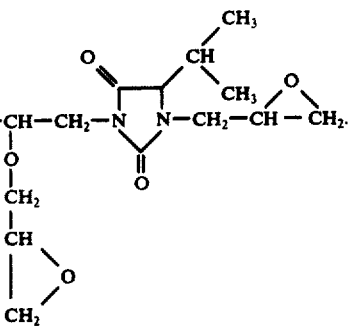

7. The curable mixture according to claim 1 wherein the polyglycidyl compound is

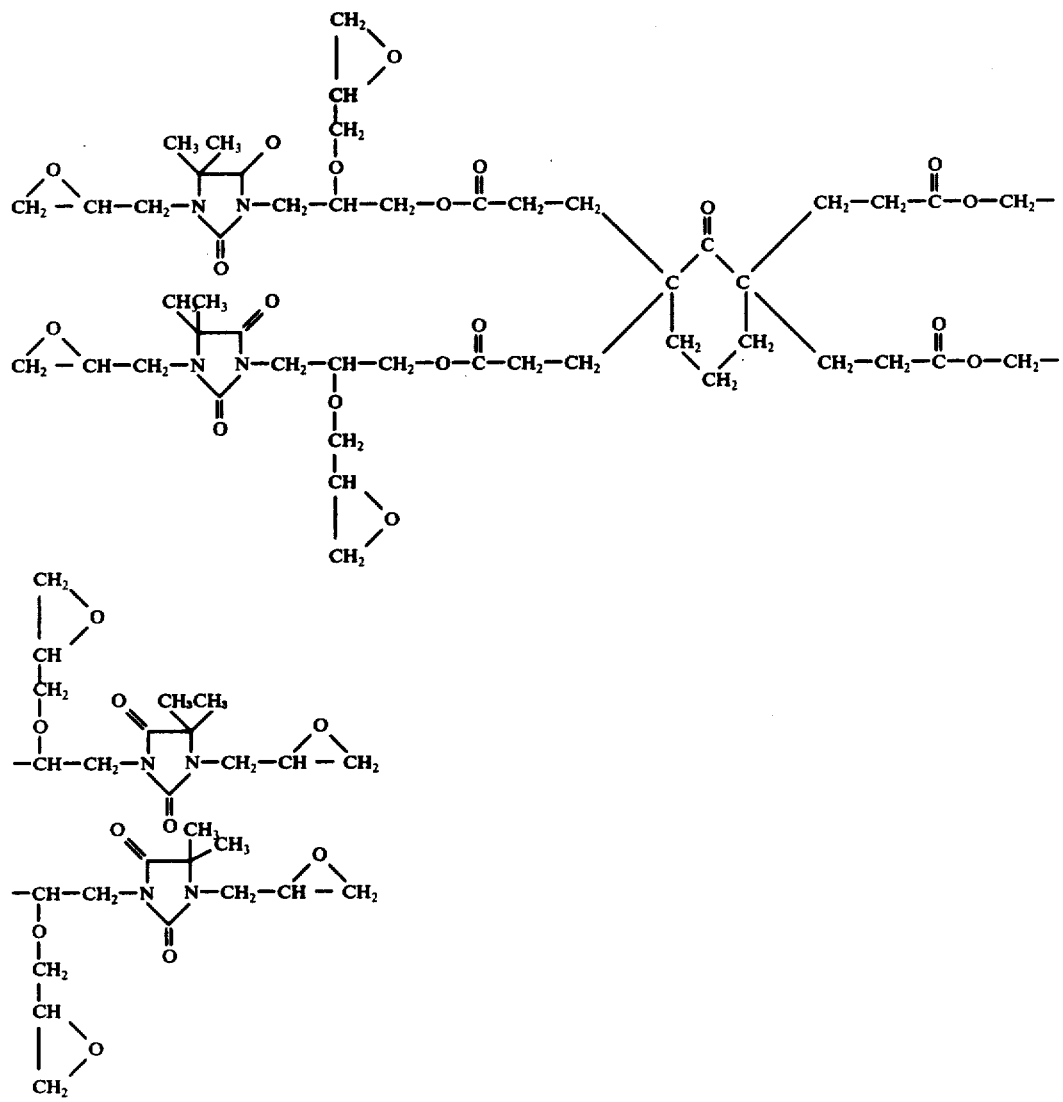

hydrogen halide acceptor and with azeotropic removal of the water.

8. The curable mixture according to claim 1 wherein said epoxy resin curing agent is a dicarboxylic acid anhydride.

9. The curable mixture according to claim 8 wherein the dicarboxylic acid anhydride is hexahydrophthalic anhydride, or phthalic anhydride.

* * * * *